large table follows:

United States Patent [19]

Juguin et al.

[11] 4,201,661

[45] May 6, 1980

[54] PROCESS FOR PRODUCING AROMATICS OF HIGH PURITY FROM OIL CUTS

[75] Inventors: Bernard Juguin; Jean-Francois Le Page, both of Rueil Malmaison; Jean Miquel, Paris, all of France

[73] Assignee: Institut Francais du Petrole, Rueil Malmaison, France

[21] Appl. No.: 454,942

[22] Filed: Mar. 26, 1974

[30] Foreign Application Priority Data

Mar. 26, 1973 [FR] France .................................. 73 10854

[51] Int. Cl.$^2$ ............................................. C10G 35/08
[52] U.S. Cl. ..................................... 208/139; 252/441; 585/419
[58] Field of Search ........................ 208/138, 139, 65; 252/441, 466 PT; 260/673.5, 673, 668; 585/419

[56] References Cited

U.S. PATENT DOCUMENTS

| | | |
|---|---|---|
| 2,752,289 | 6/1956 | Haensel ................................ 208/139 |
| 2,848,377 | 8/1958 | Webb ................................... 208/138 |
| 2,911,357 | 11/1959 | Myers et al. ......................... 208/138 |
| 3,156,735 | 11/1964 | Armstrong ..................... 252/466 PT |
| 3,567,625 | 3/1971 | Sinfelt et al. ......................... 208/139 |
| 3,585,253 | 6/1971 | Huang ............................. 252/466 PT |
| 3,617,518 | 11/1971 | Sinfelt et al. ......................... 208/138 |
| 3,729,408 | 4/1973 | Carter et al. ......................... 208/138 |
| 3,769,201 | 10/1973 | Sinfelt et al. ......................... 208/139 |
| 3,789,020 | 1/1974 | Carter et al. ................... 252/466 PT |
| 3,850,747 | 11/1974 | Sinfelt et al. ......................... 208/139 |
| 3,901,827 | 8/1975 | Sinfelt et al. ......................... 208/139 |

Primary Examiner—C. Davis
Attorney, Agent, or Firm—Millen & White

[57] ABSTRACT

Aromatic hydrocarbons of high purity are produced from saturated or unsaturated gasolines and hydrogen in the presence of a new catalyst containing alumina, platinum, at least one metal selected from the group consisting of iridium, rhodium and palladium and at least one metal selected from the group consisting of copper, silver and gold.

1 Claim, No Drawings

PROCESS FOR PRODUCING AROMATICS OF HIGH PURITY FROM OIL CUTS

This invention concerns a process for producing aromatic hydrocarbons of high purity.

By the production of aromatic hydrocarbons, is meant, for example, the production of benzene, toluene and xylenes (ortho, meta or para), either from saturated or unsaturated gasolines, for example pyrolysis or cracking gasolines, such as steam-cracking gasolines, catalytic reforming gasolines, or from naphthenic hydrocarbons which may be dehydrogenated to aromatic hydrocarbons, or also from paraffinic hydrocarbons which yield aromatic hydrocarbons by dehydrocyclization.

(A) When the aromatic hydrocarbons are produced from saturated or unsaturated gasolines, the following technique may be adopted, the following indications being not limitative.

First of all, as far as an unsaturated feed charge is concerned, i.e., containing diolefins and monoolefins, it must be made free of them, for example by selective hydrogenation (whose purpose is to eliminate diolefins and alkenylaromatics by converting them to monoolefins and alkylaromatics respectively) optionally followed, after convenient treatment of the effluent, with a hydrogenation-hydrodesulfurization, so as to convert the monoolefins to paraffins and desulfurize the feed charge.

The charge freed, when necessary, from substantially all the diolefins and monoolefins that it could contain, is fed to at least one reaction zone where it is subjected to hydrogen treating, in the presence of an appropriate catalyst which, up to now, contained a metal of group VIII and/or also a metal or compound of a metal from groups VI B and and VII B from the periodic classification of the elements, for example platinum, nickel, cobalt, palladium, iridium, ruthenium, rhenium, tungsten and molybdenum, either sulfurized or not, at a temperature of from about 400° to about 600° C., under a pressure of from 1 to 60 kg/cm$^2$, the hourly feed rate by volume of the liquid charge being about 0.1–10 times the volume of the catalyst, the molar ratio hydrogen/hydrocarbons being about 0.5–20. The hydrogen treatment may be carried out in one or more reaction zones.

The catalyst is usually a bi-functional catalyst, i.e., one comprising an acid function (the carrier) and a dehydrogenating function; the acid function is supplied by acid compounds, such as aluminae and chlorinated and/or fluorinated aluminae or other similar compounds amongst which alumina-silica, alumina-magnesia, thoria-silica, alumina-magnesia may be mentioned. The dehydrogenating function is supplied by metals of the groups VIII, VI B or VII B of the periodic classification of the elements.

(B) When the aromatic hydrocarbons are produced from a feedstock consisting of naphthenic and/or paraffinic hydrocarbons, this stock may be so treated according to well-known conventional conditions; it may also be treated substantially as hereinbefore described, possibly with the same type of catalyst. The hydrogen treatment may be carried out in one or more reaction zones.

(C) We have now found that, in order to carry out the hydrogen treatment of the feed charge and obtain aromatic products of very high purity, it is quite advantageous to use an alumina-containing catalyst characterized by both of the following features:

(a) on the one hand, it must contain platinum and at least one other metal of group VIII selected from the groups consisting of iridium, rhodium and palladium.

During the hydrogen treatment of the charge:

the iso and n.paraffins are cracked chiefly to propane, butane and iso-butane, to a lower degree to pentane, iso-pentane, hexane and iso-hexane, and additionally to ethane and methane, the naphthenes are dehydrogenated to aromatics and supply the amount of hydrogen necessary for paraffin cracking, the aromatics are not substantially modified;

(b) on the other hand, the catalyst must also contain critical amounts of at least one other metal selected from the group consisting of copper, silver and gold. The presence of at least one of these metals considerably reduces the hydrogenolyzing and dealkylating effect of the noble metals, so that the aromatic content and the hydrogen yield may be increased, said hydrogen resulting from naphthenes dehydrogenating.

The invention is thus characterized in that there is used a catalyst containing (a) alumina, (b) from 0.01 to 5% of platinum by weight with respect to alumina, (c) from 0.001 to 1%, preferably from 0.01 to 0.1%, by weight with respect to alumina, of at least one metal selected from the group consisting of iridium, rhodium and palladium and (d) from 0.0001 to 0.05% and preferably 0.001 to 0.045%, by weight with respect to alumina of at least one metal selected from the group consisting of copper, silver and gold.

The catalyst may optionally further contain from 0.1 to 10% of halogen, for example chlorine or fluorine, by weight with respect to alumina. It is essential that the catalyst contain no more than 0.05% by weight, with respect to alumina, of the metals selected from copper, silver and gold.

The atomic ratio of the main metal (platinum) to the other associated metals may be selected at will.

The surface characteristics of the catalyst carrier, i.e., alumina, are important: the specific surface of the alumina is between 50 and 600 m$^2$/g, preferably between 150 and 400 m$^2$/g, so as to operate at fairly high space velocities and avoid the use of too big reactors and too large amounts of catalyst.

When several reaction zones are employed, it may be advantageous to use a distinct catalyst in each zone. On the other hand, irrespective of the number of reaction zones, it is sometimes advantageous, in order to improve the hydrogen treatment, to divide the treatment which takes place in one of the reaction zones, into two steps ($\alpha$) and ($\beta$), each of these steps being carried out in a distinct reaction zone.

Step ($\alpha$) may be carried out at a temperature of from about 400° to about 600° C., under a preferred pressure of 1–60 kg/cm$^2$ in the presence of hydrogen and a catalyst.

Step ($\beta$) may be carried out at a temperature of from about 500° to about 600° C., under a preferred pressure of 1–60 kg/cm$^2$ in the presence of hydrogen and a catalyst.

The catalyst of step ($\alpha$) may be substantially neutral and have a specific surface lower than 100 m$^2$/g (the carrier is, for example, gamma alumina) and the catalyst of step ($\beta$) is acidic and has a relatively high specific surface (for example cubic gamma alumina or chlorinated or fluorinated aluminae). In these catalysts, the metallic elements may be identical or different in each of the steps (α) and (β) and are any one of those proposed in the invention.

(D) The catalyst may be prepared according to conventional methods consisting of impregnating the carrier by means of solutions of the desired metal compounds. Either a common solution of these metals or distinct solutions for each metal may be used. When several solutions are used, intermediary dryings and roastings may be carried out. A final roasting takes place, for example between about 500° and 1000° C., preferably in the presence of free oxygen, for example by forcing air therethrough.

As examples of copper, gold and silver compounds, we can mention the nitrates, chlorides, bromides, fluorides, sulfates or acetates of these metals or any other salt soluble in water or hydrochloric acid.

Platinum may be used in any known form, for example as hexachloroplatinic acid, ammonium chloroplatinate, platinum sulfide, sulfate or chloride. Iridium, palladium and rhodium may be used in any known form, for example as chlorides, bromides, sulfates or sulfides or, for example, in the form of hexachloroiridic acid, hexabromoiridic acid, hexafluoroiridic acid, or any other iridium, palladium or rhodium compound.

The halogen may be supplied with one of the above halides or may be used in the form of hydrogen chloride, hydrogen fluoride, ammonium chloride, ammonium fluoride, gaseous chlorine or hydrocarbon halide, for example $CCl_4$, $CHCl_3$ or $CH_3Cl$.

A first method of manufacture consists, for example, of impregnating the carrier by means of an aqueous solution of copper, gold or silver nitrate or other compound, drying at about 120° C. and roasting in air for a few hours at a temperature of from 500° to 1000° C., preferably at about 700° C.; this is followed with a second impregnation by means of a solution containing platinum and another noble metal (for example a solution of hexachloroplatinic acid or hexachloroiridic acid).

Another method consists, for example, of impregnating the carrier with a solution containing both:
(1) platinum, for example hexachloroplatinic acid,
(2) the other noble metal, for example hexachloroiridic acid,
(3) the metal(s) selected from copper, silver and gold, for example a chloride, bromide, fluoride, sulfate or acetate of the selected metal or any other salt of the selected metal soluble in water or hydrochloric acid,
(4) optionally chlorine or fluorine.

A further method consists of introducing the metal elements by carrying as many successive impregnations as the number of metal elements of the catalyst; for example, the noble metal, other than platinum, is first introduced by means of a solution containing it, optionally followed with drying and roasting, then platinum by means of a solution containing it, optionally followed with drying and roasting, and finally the metal (s) of the copper, gold and silver group, the latter impregnation being followed with drying and roasting at a temperature of, for example, about 500°–1000° C.

The above order of the impregnations is not constraining and may be modified.

(E) The hydrogen treatment may be carried out, as hereinbefore described, in at least one reaction zone, i.e. in at least one reactor. There can be used:
(1) either one or several fixed bed reactors, and possibly one replacement reactor which will be used when regenerating the catalyst of one of the fixed bed reactors,
(2) or one or several fluid bed reactors,
(3) or, and this is often one of the best solutions when a continuous operation over long periods is desired, at least one moving bed reactor; the method, as described in the French Patent Application No. 71/41069 of Nov. 16, 1971, consists of circulating the charge and hydrogen through at least one catalyst containing reaction zone, for example in the form of particles, the catalyst being progressively charged at one of the two ends of the reaction zone, and progressively discharged at the other one of the two ends of the reaction zone; the catalyst progressively discharged from the reaction zone is passed to a regeneration zone, the catalyst, once regenerated and reduced in the presence of a hydrogen stream, being progressively reintroduced at the end of the reaction zone opposite to that from which the catalyst had been discharged, so as to replace the catalyst discharged from the reaction zone and maintain a level of activity which is high and substantially constant at each point of the discharge of the catalyst from each moving bed reactor or from the moving bed reactors, when several are used, is carried out "progressively" as hereinbefore stated. By "progressively" we mean that the catalyst may be discharged:

either periodically, for example at a frequency of 1/10 to 10 days, by discharging at each time only a fraction, for example, 0.5–15% of the total amount of catalyst. It is also possible to withdraw the catalyst as a higher frequency of, for example, one minute or one second, provided the withdrawn amount is reduced in proportion, or continuously.

The moving bed reactor (s) and the regeneration zone may be located at will, for example side by side. It may be necessary to repeatedly transport the catalyst from a relatively low level to a relatively high level, for example from the bottom of a reaction zone to the top of the regeneration zone; this transport may be carried out by means of any known elevator, for example a "lift". The "lift" fluid which is used for conveying the catalyst may be any appropriate gas, for example nitrogen or hydrogen, particularly purified hydrogen.

The solid material which is so displaced through the moving bed reactor(s) may be a particular catalyst containing an appropriate carrier: this catalyst may be shaped, for example, as spherical balls whose diameter is usually between 1 and 3 mm, preferably between 1.5 and 2 mm, these values being not limiting. The bulk density of the catalyst may range, for example, from 0.4 to 1, preferably from 0.5 to 0.9, more preferably from 0.6 to 0.8, these values being not limiting.

The regeneration of the catalyst may be carried out according to any known method or according to the method described in the French Patent Application No. 71/41069 of Nov. 16, 1971.

A preferred method for treating the feed charge with hydrogen consists of passing the charge first through at least one fixed bed reactor at a temperature of from 480° to 530° C. and then through a moving bed reactor at a temperature of from 510° to 580° C.

(F) Once the charge has been treated as hereinbefore explained, the products are made free of the normally gaseous materials by any known appropriate means, for example by stripping. The products are then subjected to one or more fractionations, so as to obtain various cuts containing ethylbenzene, xylenes and $C^+_9$, and a $C_6$ and/or $C_7$ cut containing benzene (benzene fraction) and/or toluene (toluene fraction), according to what is desired. Further, up to now, it was often necessary to carry out treatments, such as extractions or extractive distillations, but these treatments are not necessary now, provided the aromatic production has been carried out according to the present invention in the presence of the hereinbefore described catalysts.

The following, non-limiting examples illustrate the invention.

EXAMPLE 1

Four catalysts A, B, C and D have been prepared; their composition by weight was the following:
A: platinum: 0.6%, iridium: 0.04%
B: platinum: 0.6%, iridium: 0.04%, copper: 0.04%
C: platinum: 0.6%, iridium: 0.04%, silver: 0.04%
D: platinum: 0.6%, iridium: 0.04%, gold: 0.04%

The carrier of these catalysts consisted of alumina balls of a 235 $m^2/g$ specific surface and a 75 $cm^3/100$ g total pore volume. The chlorine content of the catalysts was 1.2% by weight.

Catalyst C has been prepared by adding to 100 g of alumina, 100 cc of an aqueous solution containing 0.063 g of silver nitrate, 2.1 g of concentrated HCl (d=1.19), 25.5 cc of an aqueous solution of chloroplatinic acid having a 2.35% by weight content of Pt and 1.74 cc of an aqueous solution of chloroiridic acid having a 2.3% by weight content of Ir.

The contact was maintained for 5 hours, then we have discharged the solid material, dried it at 100° C. for one hour and calcined it for 4 hours at 530° C. in dry air (dried with activated alumina). Then we have reduced in a stream of dry hydrogen (activated alumina) for 2 hours at 450° C. The resulting catalyst contained, by weight with respect to the catalyst carrier: 0.6% of platinum, 0.04% of iridium, 0.04% of silver and 1.2% of chlorine.

The catalyst C had a specific surface of 230 $m^2/g$ and a pore volume of 70 cc/100 g.

The catalyst B has been prepared by adding to 100 g of alumina, 100 cc of an aqueous solution containing:
0.152 g of copper nitrate tri-hydrato
2.10 g of concentrated HCl (d=1.19)
25.5 cc of an aqueous solution of chloroplatinic acid containing 2.35% by weight of platinum,
and 1.74 cc of an aqueous solution of chloroiridic acid containing 2.3% by weight of iridium.

The contact was maintained for 5 hours, then we separated the liquid, we dried the solid for 1 hour at 100° C. and we calcined at 530° C. in dry air (dried by means of activated alumina). Then we reduced in a dry hydrogen stream (activated alumina) for 2 hours at 450° C. The catalyst finally contained, by weight with respect to the catalyst carrier, 0.6% of platinum, 0.04% of iridium, 0.04% of copper and 1.2% of chlorine.

The catalysts A and D, and those of the following examples, have been prepared according to similar methods which will not be described in greater detail.

These four catalysts have been successively introduced into 3 reactors, so as to constitute 3 catalyst beds:
first bed: 10% by volume of the catalyst,
second bed: 15% by volume of the catalyst
third bed: 75% by volume of the catalyst.

The first two reactors were of the fixed bed type. The third reactor was a moving bed reactor which was operated according to the regenerative technique. In the third reactor, the catalyst was in the form of balls; it was continuously discharged from the reactor at a hourly rate of about 1/400 of the total amount of catalyst in the reactor. Then the catalyst discharged from the bottom of the reactor was conveyed by means of a mechanical elevator ("lift") to an "accumulator-decanter" tank in which the conveying gas was separated from the catalyst. The used catalyst accumulated in the "accumulator-decanter" tank before feeding a regenerator located below this tank: at regular intervals, the regenerator was equilibrated in pressure with the "accumulator-decanter" tank. It was then filled with catalyst supplied through a valve system from the "accumulator-decanter" tank and isolated from the remainder of the plant. When necessary, the regenerator was purged with nitrogen, so as to eliminate the hydrocarbons carried along the lift. Then the regeneration took place in fixed bed in 3 successive steps, according to the method described in the French Patent Application No. 71/41 069 of Nov. 16, 1971:

(1) in a first step, coke was burnt: the temperature at the inlet of the regenerator was maintained at 440° C., the pressure in the regenerator at 5 $kg/cm^2$ absolute and the oxygen proportion at the regenerator inlet at 0.3% by volume, the operation being continued for 1 h 30 mn, (2) in a second step, an oxychlorination took place with the simultaneous injection of oxygen and C $Cl_4$: the temperature was maintained at 510° C. at the regenerator inlet, the pressure at 5 $kg/cm^2$ abs. in the regenerator, the oxygen proportion at the regenerator inlet at 2-2.5% by volume, the $CCl_4$ injection being carried out at a rate of 3.4 kg per hour. This step was continued for 1 hour, (3) in a third step, a second oxidation took place: the temperature was maintained at 510° C., the pressure at 5 $kg/cm^2$ abs., the oxygen proportion at 4.5-6% by volume at the reactor inlet; the step was continued for 1 hour.

After this third step, the regenerator was purged with nitrogen, and then balanced in pressure with the third reactor. The catalyst was conveyed by means of a lift from the regenerator to this reactor. Above this reactor, in an independent tank, the catalyst was reduced with a hydrogen stream (hydrogen flow rate: 25 kg per hour) at 500° C. under a pressure of 13 $kg/cm^2$ abs. Then an amount of fresh catalyst was progressively introduced into this reactor at a hourly rate of about 1/400 of the total amount of catalyst in the reactor.

In order to produce benzene, a $C_6$ cut and hydrogen were passed over each of these 3 catalysts, said cut having the following characteristics:
density: at 15° C.: 0.689
ASTM distillation: I.P. 65° C.; F.P. 85° C.
the composition by weight of the $C_6$ cut was the following:

| n-hexane | 69.55% |
| n-heptane + iso-heptanes | 2.82% |
| methylcyclopentane | 13.82% |
| cyclohexane | 9.67% |
| benzene | 4.14% |

The operating conditions for the 3 reactors were:
First bed temperature: 520° C.
Second bed temperature: 520° C.
Third bed temperature: 550° C.
Pressure: 10 bars Liquid hourly feed rate: 3 times the volume of the catalyst Molar ratio hydrogen/hydrocarbons at the inlet of each reactor: 5

The product discharged from the third reactor consisted of a liquid phase and a gas phase which were analyzed by mass spectrometry and gas phase chromatography. The results are given in table I, they are expressed in % by weight per 100 g of initial charge.

TABLE I

| Constituents Catalyst | A | B | C | D |
|---|---|---|---|---|
| Hydrogen | 1.17 | 2.06 | 2 | 2.02 |
| Methane | 4.54 | 3.50 | 2.87 | 2.91 |
| Ethane | 11.38 | 7.71 | 7.20 | 7.17 |
| Propane | 17.71 | 13.93 | 13.05 | 13.10 |
| Isobutane | 8.27 | 6.58 | 7.11 | 7.09 |
| n butane | 10.05 | 9.43 | 10.02 | 10.01 |
| Isopentane | 3.22 | 4.29 | 4.91 | 4.93 |
| n pentane | 2.37 | 3.08 | 3.68 | 3.71 |
| Σ n hexane + isohexanes | 1.07 | 1.50 | 3.63 | 2.98 |
| Σ n heptane + isoheptanes | 0.02 | 0.037 | 0.13 | 0.11 |
| Methylcyclopentane | 0.05 | 0.079 | 0.213 | 0.166 |
| Cyclohexane | 0.003 | 0.004 | 0.004 | 0.004 |
| Benzene | 37.48 | 45.35 | 42.34 | 43.10 |
| Toluene | 2.07 | 1.95 | 1.98 | 1.96 |
| Ethylbenzene | 0.06 | 0.053 | 0.099 | 0.10 |
| Σ xylenes | 0.32 | 0.26 | 0.46 | 0.42 |
| Σ $C_9$ aromatics | 0.057 | 0.037 | 0.11 | 0.09 |
| Σ $C_{10}$ aromatics | 0.16 | 0.16 | 0.12 | 0.13 |
| $C_5^+$ yield by weight | 46.88% | 56.79% | 57.75% | 57.70% |

It may be observed, also by comparing with the following example I A, that it is advantageous to use the catalysts of the invention, i.e. those containing at least one third metal associated with a pair of noble metals; the benzene production is increased, as well as the hydrogen production.

After separation of the normally gaseous products, we have distilled 10 kg of the liquid phase obtained with catalyst B, by using a 70 plate tower whose reflux ratio was 35.

We have discharged 0.8 kg of product whose composition by weight was:

| Benzene | 73.12% |
|---|---|
| butanes | 1.353% |
| pentanes | 7.82% |
| hexanes | 16.27% |
| heptanes | 0.39% |
| Cyclohexane | 0.029% |
| Methylcyclopentane | 0.99% |
| Toluene | 0.018% |

These 0.8 kg were recycled to the inlet of the catalyst bed.

The bottoms were rectified in a second 50 plate tower at a reflux ratio of 3. Benzene was discharged from the top of the column; its content of non-aromatic impurities was 85 ppm by weight.

EXAMPLE 2

We have prepared three catalysts E, F, G whose compositions was the following:
E: platinum: 0.6%; palladium: 0.04%
F: platinum: 0.6%; palladium: 0.04%; copper: 0.03%
G: platinum: 0.06%; palladium: 0.04%; silver: 0.04%

These metals have been incorporated to the same alumina balls as used in example 1; the chlorine content was 1.2% for each catalyst.

We have used the technique of example 1, as applied to the production of toluene: we have passed over each of the three catalysts hydrogen and a $C_7$ cut of the following characteristics:
density at 15° C.: 0.727
distillation ASTM: IP: 85° C.; FP: 110° C.
Its composition by weight was the following:

| isoheptanes | 18.80% |
|---|---|
| n heptane | 27.14% |
| isooctanes | 4.65% |
| $C_7$ naphthenes | 41.65% |
| $C_8$ naphthenes | 2.52% |
| toluene | 5.24% |

The process conditions were the following for the three catalysts:
temperature of the first bed: 520° C.
temperature of the second bed: 520° C.
temperature of the third bed: 545° C.
pressure: 10 bars
liquid charge hourly feed rate: 3 times the volume of the catalyst
molar ratio of the hydrogen to the hydrocarbons: 5 at the inlet of each reactor.

TABLE II

| Constituents Catalysts | E | F | G |
|---|---|---|---|
| Hydrogen | 3.17 | 3.77 | 3.33 |
| Methane | 2.36 | 0.87 | 1.15 |
| Ethane | 2.74 | 2.31 | 3.02 |
| Propane | 5.78 | 4.94 | 6.45 |
| Isobutane | 4.36 | 2.86 | 3.75 |
| n butane | 6.28 | 4.12 | 5.39 |
| isopentane | 2.04 | 1.33 | 1.73 |
| n pentane | 1.50 | 0.97 | 1.27 |
| Σ n hexane + isohexanes | 0.72 | 0.41 | 0.43 |
| Σ n heptane + isoheptanes | 1.31 | 1.67 | 1.38 |
| Σ n octane + isooctanes | 0.11 | 0.12 | 0.11 |
| Methylcyclopentane | 0.03 | 0.07 | 0.06 |
| Benzene | 3.20 | 0.61 | 0.76 |
| Toluene | 60.35 | 68.89 | 65.15 |
| Ethylbenzene | 0.28 | 0.68 | 0.54 |
| Σ Xylenes | 5.43 | 5.80 | 5.01 |
| Σ $C_9$ aromatics | 0.27 | 0.25 | 0.25 |
| Σ $C_{10}$ aromatics | 0.07 | 0.33 | 0.22 |
| $C_5^+$ yield by weight | 75.31% | 81.13% | 76.91% |

The product discharged from the last reactor has been analyzed by mass spectrometry and gas phase chromatography. The results are given in Table II in % by weight with respect to 100 g of initial feed charge.

The advantage resulting from the use of the catalysts according to the invention may also be observed: the toluene and hydrogen productions are substantially increased, and substantially less methane and ethane is formed.

After separation of the normally gaseous products, we have distilled 10 kg of the liquid phase obtained by means of catalyst F. We have used a 70 plate tower operated at a reflux ratio of 20. We have discharged from the top of the tower 0.65 kg of product which was recycled to the inlet of the catalyst bed. This topping product contained benzene, some toluene, paraffins lower than $C_8$ and methyl cyclopentane. The bottoms product was rectified in a second 40 plate t wer at a reflux ratio of 2.5. We have discharged toluene from the top, the content of non-aromatic impurities of which was 95 ppm by weight.

EXAMPLE 3

Three catalysts H, I and J were prepared, their composition by weight being:
H: platinum: 0.6%; rhodium: 0.04%
I: platinum: 0.6%; rhodium: 0.04%; gold: 0.03%
J: platinum: 0.6%; rhodium: 0.04%; copper: 0.02%

These metals were incorporated to the alumina balls of example 1, the chlorine content being 1.2% for the three catalysts.

The technique of example 1 was used for producing $C_8$ aromatics (xylenes and ethylbenzene). A cut was passed with hydrogen over the three catalysts, the properties of which were:
density at 15° C.: 0.741
ASTM distillation: IP: 110; FP: 140
Its composition by weight was:
n octane + isooctanes: 44.52%
n nonane + isononanes: 16.42%
$C_8$ naphthenes: 24.05%
$C_9$ naphthenes: 2.42%
Ethylbenzene: 2.84%
xylenes: 9.75%

The operating conditions for the three catalysts were the following:
temperature of the first bed: 515° C.
temperature of the second bed: 515° C.
temperature of the third bed: 535° C.
pressure: 10 bars
hourly feed rate of the liquid charge: 3 times the catalyst volume
molar ratio of the hydrogen to the hydrocarbons: 5 at the inlet of each reactor.

The product discharged from the last reactor has been analyzed by mass spectrometry and gas phase chromatography. The results, expressed in % by weight with respect to 100 g of the initial charge, are given in table III.

After separation of the normally gaseous products, we have distilled 10 kg of the liquid phase obtained by means of catalyst I. In a first column, benzene and $C_4$–$C_8$ paraffins were separated; toluene was separated in a second column and the bottoms product of the second column were rectified in a third 40 plate column at a reflux ratio of 2.5. There was obtained, as top product, a mixture of $C_8$ aromatics (ethylbenzene and xylenes) whose non-aromatic impurity content was 20 ppm by weight.

EXAMPLE 4

For producing simultaneously benzene and $C_8$ aromatics (ethylbenzene and xylenes) we have passed over the three catalysts A, B and C of example 1, hydrogen and a cut defined as follows:
density at 15° C.: 0.731
distillation ASTM: IP 65° C.; FP 145° C.
Its composition by weight was:
n hexane + isohexanes: 12.80%
n heptane + isoheptanes: 21.58%
n octane + isooctanes: 29.76%
n nonane + isononanes: 10.65%
Methylcyclopentane: 2.24%
cyclohexane: 1.51%
$\Sigma C_7$ naphthenes: 6.16%
$\Sigma C_8$ naphthenes: 4.50%
$\Sigma C_9$ naphthenes: 3%
Benzene: 0.57%
Toluene: 2.65%
Ethylbenzene: 0.87%
$\Sigma$Xylenes: 3.71%

The operating conditions were the following for the three catalysts:
temperature of the first bed: 515° C.
temperature of the second bed: 515° C.
temperature of the third bed: 545° C.
pressure: 10 bars
liquid charge hourly feed rate: 3 times the volume of the catalyst

TABLE III

| CONSTITUENTS / CATALYSTS | H | I | J |
| --- | --- | --- | --- |
| Hydrogen | 3.22 | 3.80 | 3.38 |
| Methane | 1.56 | 0.71 | 1.14 |
| Ethane | 2.16 | 1.05 | 1.69 |
| Propane | 4.99 | 2.83 | 4.55 |
| Isobutane | 3.99 | 1.71 | 2.75 |
| n butane | 5.68 | 2.45 | 3.93 |
| isopentane | 2.29 | 0.84 | 1.35 |
| n pentane | 1.66 | 0.60 | 0.97 |
| $\Sigma$ n hexane + isohexanes | — | 0.43 | 0.22 |
| $\Sigma$ n heptane + isoheptanes | — | 0.15 | 0.08 |
| $\Sigma$ n octane + isooctanes | — | 0.04 | 0.02 |
| Methylcyclopentane | — | 0.04 | — |
| Benzene | 5.88 | 0.70 | 2.36 |
| Toluene | 20.04 | 1.33 | 4.54 |
| Ethylbenzene | 1.11 ⎫ | 11.10 ⎫ | 7.65 ⎫ |
| $\Sigma$ Xylenes | 39.69 ⎬ 40.80 | 57.85 ⎬ 68.95 | 53.70 ⎬ 61.35 |
| $\Sigma$ $C_9$ aromatics | 7.10 | 14.01 | 11.25 |
| $\Sigma$ $C_{10}$ aromatics | 0.63 | 0.36 | 0.42 |
| $C_5^+$ yield by weight | 78.40% | 87.45% | 82.56 |

Here again, the substantial advantage of using the catalysts according to the invention may be observed: the production of $C_8$ aromatics considerably increased and the catalysts were by far less cracking (less methane, ethane, propane, butane and pentanes) and less dealkylating (substantially less toluene and benzene).

hydrogen/hydrocarbons molar ratio: 5 at the inlet of each reactor.

The product discharged from the last reactor has been analyzed by mass spectrometry and gas phase chromatography. The results, expressed in % by weight with respect to 100 g of the initial charge, are given in table IV.

The great advantage of using the catalysts of the

TABLE IV

| Constituents Catalysts | A | B | C |
|---|---|---|---|
| Hydrogen | 2.74 | 3.46 | 3.14 |
| Methane | 3.16 | 1.36 | 1.88 |
| Ethane | 3.95 | 3.02 | 3.10 |
| Propane | 7.87 | 6.68 | 6.61 |
| isobutane | 5.34 | 3.69 | 4.07 |
| n butane | 7.61 | 5.27 | 5.81 |
| isopentane | 3.77 | 2.01 | 2.42 |
| n pentane | 2.73 | 1.45 | 1.75 |
| n hexane + isohexanes | 0.25 | 0.73 | 0.58 |
| n heptane + isoheptanes | 0.17 | 0.22 | 0.20 |
| n octane + isooctanes | 0.01 | 0.03 | 0.03 |
| Methylcyclopentane | 0.01 | 0.02 | 0.02 |
| Benzene | 9.68 | 8.92 | 9.17 |
| Toluene | 26 | 21.44 | 23.32 |
| Ethylbenzene | 1.50 | 4.78 | 3.52 |
| Xylenes | 18.68 | 27.40 | 25.37 |
| $C_9$ aromatics | 6.23 | 9.26 | 8.74 |
| $C_{10}^+$ aromatics | 0.30 | 0.26 | 0.27 |
| $C_5^+$ yield by weight | 69.33% | 76.52% | 75.39% |
| benzene + $C_8$ aromatics | 29.86% | 41.10% | 38.06% | invention may also be observed: the joint production of benzene and $C_8$ aromatics is far higher, as well as the hydrogen production.

After separation of the normally gaseous products, we have distilled 10 kg of the liquid phase obtained with catalyst B. The liquid phase was fed to a first 70 plate column at a reflux ratio of 35. 0.48 kg of products were discharged from the top and recycled to the catalyst bed inlet.

The bottoms were fed to a second 50 plate column at a reflux ratio of 3; benzene was discharged from the top of the column; its content of non-aromatic impurities was 95 ppm by weight. The bottoms were passed to a third 40 plate column at a reflux ratio of 2.5; toluene containing 60 ppm by weight of non-aromatic impurities was discharged from the top. The bottoms were fed to a fourth 40 plate column operated at a reflux ratio of 2.5. A mixture of $C_8$ aromatics (ethylbenzene and xylene) containing 40 ppm by weight of non-aromatic impurities was discharged from the top.

EXAMPLE I A

By way of comparison, we have repeated example 1 with the catalysts K-P prepared according to methods similar to those of example 1. The catalysts K-P all contained 1.2% of chlorine. The compositions by weight of the catalysts K-P with respect to the catalyst carrier were the following:

K: 0.64% of platinum + 0.04% of copper
L: 0.64% of platinum + 0.04% of silver
M: 0.64% of platinum + 0.04% of gold
N: 0.64% of iridium + 0.04% of copper
O: 0.64% of iridium + 0.04% of silver
P: 0.64% of iridium + 0.04% of gold The product discharged from the last reactor, by using each of the catalysts, consisted of a liquid phase and a gas phase which have been analyzed by mass spectrometry and gas phase chromatography. The results are given in table V; they are expressed in % with respect to 100 g of initial charge.

TABLE V

| CONSTITUENTS CATALYSTS | K | L | M | N | O | P |
|---|---|---|---|---|---|---|
| Hydrogen | 1.97 | 1.80 | 1.89 | 1.57 | 1.21 | 1.24 |
| Methane | 3.17 | 3.11 | 3.16 | 8.51 | 9.46 | 9.59 |
| Ethane | 5.19 | 4.96 | 4.90 | 10.25 | 11.20 | 11.17 |
| Propane | 15.48 | 15.37 | 15.42 | 12.15 | 12.70 | 12.87 |
| Isobutane | 7.74 | 7.40 | 7.29 | 4.95 | 5.18 | 5.11 |
| n butane | 11.12 | 10.26 | 10.08 | 7.13 | 7.43 | 7.36 |
| Isopentane | 4.08 | 4.15 | 4.22 | 5.55 | 5.31 | 4.99 |
| n pentane | 2.97 | 3.02 | 3.09 | 3.71 | 3.54 | 3.32 |
| Σ n hexane + isohexanes | 3.62 | 7.33 | 6.51 | 0.66 | 0.95 | 0.82 |
| Σ n heptane + isoheptanes | 0.18 | 0.38 | 0.31 | 0.01 | 0.02 | 0.02 |
| Methylcyclopentane | 0.32 | 0.47 | 0.40 | 0.03 | 0.04 | 0.03 |
| Cyclohexane | 0.10 | 0.11 | 0.09 | 0.00 | 0.01 | 0.01 |
| Benzene | 41.84 | 39.35 | 40.35 | 43.85 | 41.16 | 41.73 |
| Toluene | 1.60 | 1.66 | 1.68 | 1.29 | 1.33 | 1.32 |
| Ethylbenzene | 0.06 | 0.08 | 0.07 | 0.04 | 0.05 | 0.05 |
| Σ xylenes | 0.32 | 0.37 | 0.35 | 0.19 | 0.24 | 0.22 |
| Σ $C_9$ aromatics | 0.04 | 0.07 | 0.07 | 0.02 | 0.04 | 0.04 |
| Σ $C_{10}$ aromatics | 0.20 | 0.11 | 0.12 | 0.09 | 0.13 | 0.11 |
| $C_5^+$ yield by weight | 53.33% | 57.10% | 57.30% | 55.44% | 52.82% | 52.66% |

EXAMPLE I B

In order to show the influence of the third metal element of the catalyst according to the invention, example 1 was repeated by using various catalysts containing various copper proportions. The catalysts Q-T all contained 0.6% of platinum, 0.04% of iridium and 1.2% of chlorine.

The catalyst Q contained 0.001% of copper
The catalyst R contained 0.01% of copper
The catalyst S contained 0.047% of copper
The catalyst T contained 0.06% of copper The results are given in table VI; they are expressed in % by weight with respect to 100 g of initial charge; the results obtained with catalyst B containing 0.04% of copper are given for comparison.

TABLE VI

| CONSTITUENTS | CATALYSTS | Q | R | B | S | T |
|---|---|---|---|---|---|---|
| Hydrogen | | 1.35 | 1.99 | 2.06 | 1.67 | 1.27 |
| Methane | | 4.39 | 3.78 | 3.50 | 2.57 | 2.07 |
| Ethane | | 10.83 | 8.79 | 7.71 | 6.33 | 5.76 |
| Propane | | 18.20 | 15.40 | 13.93 | 14.72 | 15.87 |
| Isobutane | | 7.74 | 6.32 | 6.58 | 8.07 | 8.55 |
| n butane | | 9.26 | 9.08 | 9.43 | 11.62 | 12.32 |
| Isopentane | | 3.58 | 4.17 | 4.29 | 4.05 | 3.88 |
| n pentane | | 2.38 | 2.78 | 3.08 | 2.70 | 2.58 |
| Σ n hexane + isohexanes | | 1.15 | 1.41 | 1.50 | 6.04 | 9.44 |
| Σ n heptane + isoheptanes | | 0.02 | 0.03 | 0.037 | 0.67 | 0.85 |
| Methylcyclopentane | | 0.05 | 0.07 | 0.079 | 1.27 | 2.20 |
| Cyclohexane | | 0.003 | 0.004 | 0.004 | 0.24 | 0.43 |
| Benzene | | 38.45 | 43.67 | 45.35 | 38.02 | 33.05 |
| Toluene | | 2.02 | 1.98 | 1.95 | 1.62 | 1.40 |
| Ethylbenzene | | 0.06 | 0.05 | 0.053 | 0.04 | 0.03 |
| Σxylenes | | 0.31 | 0.28 | 0.26 | 0.22 | 0.17 |
| Σ $C_9$ aromatics | | 0.05 | 0.04 | 0.037 | 0.02 | 0.02 |
| Σ $C_{10}$ aromatics | | 0.16 | 0.16 | 0.16 | 0.13 | 0.11 |
| $C_5^+$ yield by weight | | 48.23% | 54.64% | 56.79% | 55.02% | 54.16% |

What we claim is:

1. A process for producing aromatic hydrocarbons from saturated or unsaturated gasolines, in the presence of hydrogen and a catalyst, in at least one reaction zone, each reaction zone being divided into successive steps (α) and (β) wherein step (α) is conducted at 400°–600° C. under a pressure of 1 to 60 kg/cm$^2$, with a substantially neutral γ-alumina catalyst having a specific surface less than 100 m$^2$/g, and step (β) is conducted at 500°–600° C. under a pressure of 1 to 60 kg/cm$^2$, with an acidic catalyst, of cubic γ-alumina or chlorinated or fluorinated alumina each step being conducted at an hourly feed rate by volume of the liquid charge of about 0.1–10 times the volume of the catalyst, in the presence of a catalyst containing (a) alumina, (b) 0.01–5% by weight of platinum with respect to alumina, (c) 0.001–1% by weight with respect to alumina of at least one metal selected from the group consisting of rhodium and palladium, and (d) 0.0001–0.05% by weight with respect to alumina of at least one metal selected from the group consisting of copper, silver and gold.

* * * * *